United States Patent [19]

Mathieu

[11] Patent Number: 4,878,516

[45] Date of Patent: Nov. 7, 1989

[54] ARRANGEMENT FOR PERITONEAL DIALYSIS AND CONNECTOR THEREFORE

[75] Inventor: Bernd Mathieu, Spiessen-Elfersberg, Fed. Rep. of Germany

[73] Assignee: Fresenius AG, Fed. Rep. of Germany

[21] Appl. No.: 256,165

[22] Filed: Oct. 7, 1988

Related U.S. Application Data

[63] Continuation of Ser. No. 850,855, Apr. 11, 1986, abandoned.

[30] Foreign Application Priority Data

Apr. 12, 1985 [DE] Fed. Rep. of Germany ....... 3513204

[51] Int. Cl.$^4$ .............................................. A61M 5/14
[52] U.S. Cl. .................................. 137/240; 251/149.1; 210/234; 210/239; 604/29; 604/33; 604/905
[58] Field of Search ................ 210/234, 321.69, 257.2, 210/239; 604/29, 30, 33, 34, 247, 249, 905; 137/240, 798, 846, 849; 251/149.1, 149.2, 149.6

[56] References Cited

U.S. PATENT DOCUMENTS

| 4,239,041 | 12/1980 | Popovich et al. | 604/29 X |
| 4,338,933 | 7/1982 | Bayard et al. | 604/905 X |
| 4,387,879 | 6/1983 | Tauschinski | 251/149.1 |
| 4,626,245 | 12/1986 | Weinstein | 251/149.1 |

FOREIGN PATENT DOCUMENTS

3210148 9/1983 Fed. Rep. of Germany .

Primary Examiner—W. Gary Jones
Attorney, Agent, or Firm—Poms, Smith, Lande & Rose

[57] ABSTRACT

A two-bag system (2) for peritoneal dialysis comprises a female connector piece (4) which is connected via a tube (28) to a peritoneal catheter. The female connector piece (4) can be connected to a male connector piece (6) to permit introduction of fresh dialysis solution from a full bag (12) into the peritoneal cavity. For receiving used dialysis solution or for receiving flushing solution accumulating prior to the dialysis operation, an empty bag (38) is provided which is connected via a further tube (36) to the male connector piece (6). The female connector piece (4) comprises a shutoff member (32) which in a predetermined connection state of the connector is opened by a central tube section (16) of the male connector piece (6). By arranging a second connection (34) on the male connector piece (6) in cooperation with the closure member (32) and a radial opening (23) in the central tube section (16) a fluid connection is possible to the two bags (12, 38) and the peritoneal cavity.

6 Claims, 4 Drawing Sheets

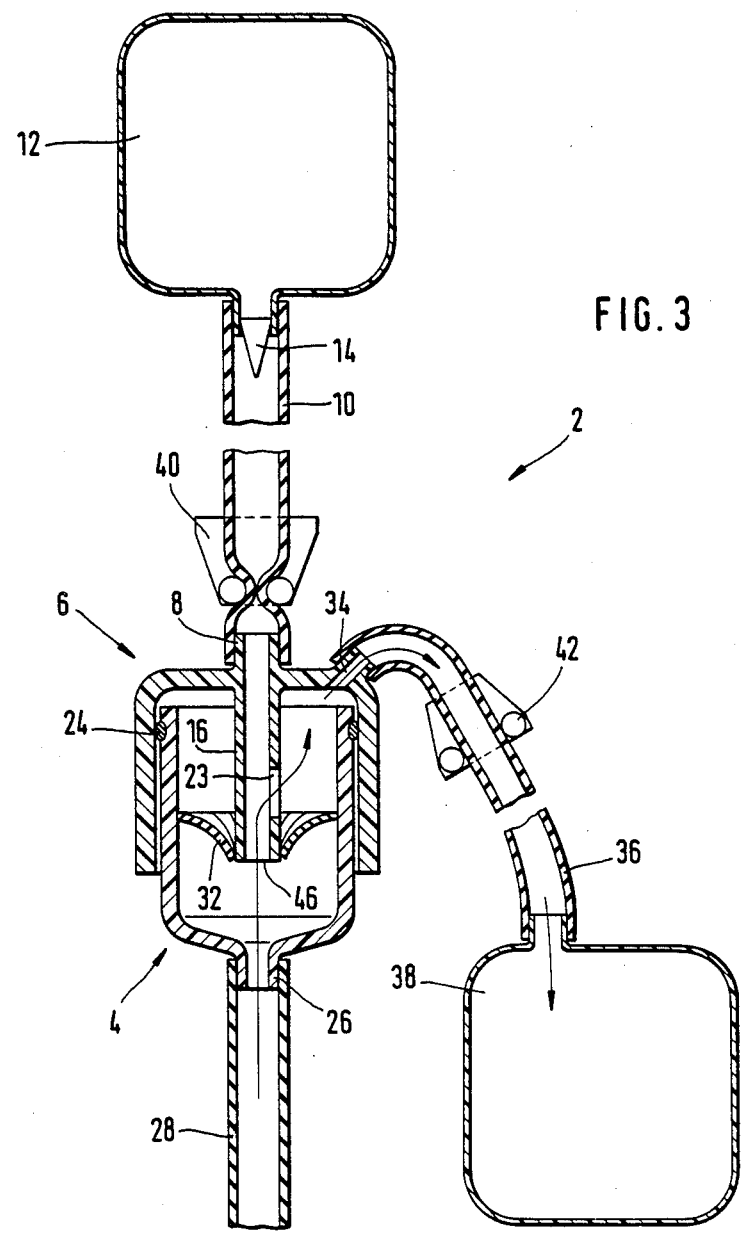

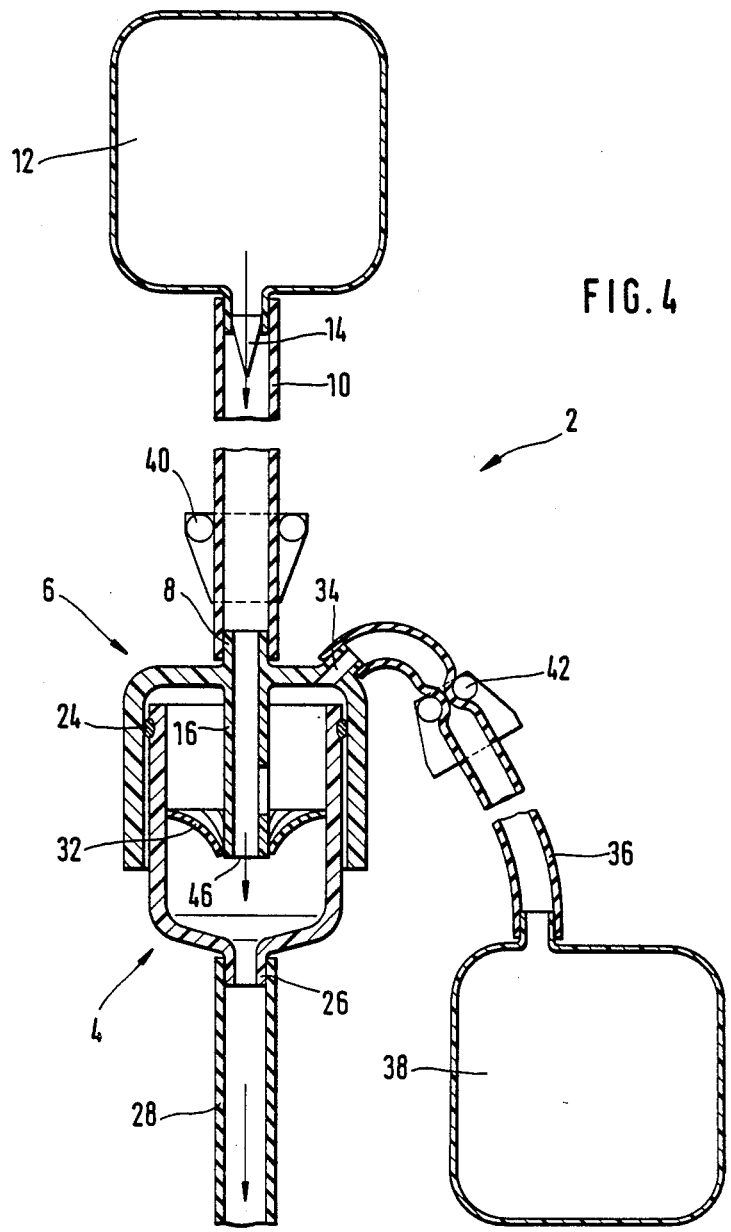

ARRANGEMENT FOR PERITONEAL DIALYSIS AND CONNECTOR THEREFORE

This is a continuation of co-pending application Ser. No. 850,855 filed on Apr. 11, 1986, now abandoned.

The invention relates to an arrangement for peritoneal dialysis and a connector therefor.

As is known, patients with kidney diseases in the final stage of their illness can be kept alive only with the aid of hemodialysis or peritoneal dialysis. Recently, peritoneal dialysis has again become the predominant technique because a method has been developed which can be carried out continuously and ambulant. In this so-called CAPD method (continual ambulant peritoneal dialysis) incontrast to hemodialysis, in which the patient at intervals of two to three days must be connected to a hemodialysis apparatus with an extracorporeal blood cycle, a catheter is implanted in the peritoneum of the patient, the end of said catheter projecting through the abdominal wall. Said end is connected during the peritoneal dialysis at certain intervals to a bag which contains a sterile dialysis solution.

Normally, the metabolism products to be separated by the kidneys, such as urea and the like, are withdrawn through the dialysis solution dialytically through the peritoneum which is thus employed as semipermeable membrane. The connection of the bag with the dialysis solution to the catheter is via a connector, a female connector piece remaining permanently connected to the catheter and being carried by the patient and a male connection piece adapted to be connected in sterile manner to the female connector piece being disposed at the end of a length of flexible tubing of a bag filled with the dialysis solution concerned.

In the two-bag system according to the preamble the used dialysis solution is drained from the peritoneum in that between the male connector piece and the filled bag a Y piece is arranged in such a manner that at the free connection of the Y piece an empty bag can be connected. Between the female connector piece and the abdomen entrance, between the Y piece and the peritoneal catheter and between the Y piece and the empty bag, in each case a shutoff member is disposed for example in the form of a roller clamp. By corresponding closing and opening of said roller clamp the following fluid passages can thus be opened and closed:

From the full bag through the connector to the peritoneum; from the full bag through the connector to the empty bag; and from the peritoneum to the empty bag.

Absolute sterility is one of the most important basic requirements when carrying out a CAPD to avoid infections due to germs introduced. On the side of the male connector piece which is connected via the flexible tube to the full bag no problems are encountered in this respect because the male connector piece can be made in sterile manner with the full bag in a unit and packed sterile and disposed of after being used once or sterilized between two uses if the flexible tube member can be separated from the bag. However, the female connector piece, which is permanently connected to the peritoneal cateter and consequently must be carried by the patient on the body, requires thorough disinfection before and after each dialysis and this is achieved for example in that with the connection between the female connector piece and the Y piece closed the female connector piece is filled or injected with a suitable disinfectant and thereafter sealed with a cover closing in sterile manner. These disinfectants are not always physiologically neutral and consequently prior to the dialysis operation a thorough flushing of the female connector piece is necessary and this is achieved for example by conducting fresh sterile dialysis solution from the full bag with the connection between the Y piece and the peritoneal catheter closed firstly via the connector and the Y piece into the empty bag so that the disinfectant in the female connector together with any residual particles which can form when the full bag is opened (for example by breaking a breakage cone) are flushed into the empty bag.

The problem arises here that in the connection of the Y piece leading to the peritoneal catheter a certain dead space remains via which the dialysis solution flows from the full bag towards the empty bags so that residues of disinfectant or particles and entrained germs can remain in this region, which is very difficult to flush. Thus, to ensure a satisfactory flushing of the entire system flushing must be carried out for a relatively long time with abundant dialysis solution. This unnecessarily lengthens the overall dialysis operation and causes a considerable consumption of dialysis solution for pure flushing purposes.

A means of this type according to the preamble is known from EP-OS 29 526 which comprises a simple unprotected connector in which two connector pieces to be contacted with the fingers are plugged. Said connector pieces each have a joining piece for flexible tubing, one of the two connector pieces comprising additionally a further connection which thus branches in Y-shaped manner from the main fluid passage. In this respect this arrangement thus does not differ from the arrangement described above so that in the tubing system dead spaces remain or residues of disinfectant and this is not without risk to the patient.

Furthermore, Germany utility model 7,834,790 and EP-OS 116 986 discloses connectors for peritioneal dialysis which however each have only one connection, i.e. in the connected state do not permit flushing or removal of dialysis solution.

The invention is therefore based on the problem of further developing the arrangement mentioned at the beginning and the connector so that a sterile connection and flushing of the entire tubing arrangement and the connector free from contaminations are possible.

According to the invention the Y piece with all its advantages is dispensed with in that a third connection for the empty bag for receiving the flushing liquid or used dialysis solution is arranged on the male connector piece separate from the connection for the fresh dialysis solution.

Advantageously, the female connector piece comprises a shutoff member which normally closes the fluid passage from the full bag to the peritoneum. Thus, by this shutoff means in the first phase of the connection of the male and of the female connector piece a closed space is created which has a supply (from the full bag) and a discharge (to the empty bag) and is partially filled with the disinfectant which is disposed in the female connector piece above the shutoff member. In this first phase the central tube section of the male connector piece does not yet open the shutoff member. An opening of the full bag, for example by breaking a breakage cone of a closure means in the connecting line now effects that fresh dialysis solution from the full bag enters the closed space through the first connection. Disinfectant and particles in this closed space are now flushed by the inflowing fresh dialyzing solution through the third connection on the male connector piece into the empty bag. Since said closed space is bordered all round by plane surfaces, no dead spaces remian in which residues of the disinfectant or germs can remain for any appreciable time and consequently the removal of the disinfectant and flushing of said space is effected with a minimum expenditure of time and flushing solution.

To prevent the formation of dead space in the connector the female connector piece advantageously comprises in the region of its introduction opening, i.e. in the region which is introduced into the male connector piece, a sealing member which is disposed in the immediate vicinity of the introduction opening so that the closed space forming when the female and male connector piece are introduced into each other is substantially free from undercuttings.

The respective susidiary claims contain advantageous further developments of the invention.

Further details, features and advantages of the present invention will be apparent from the following description of an embodiment with the aid of the drawings, wherein:

FIG. 3 shows a second connecting phase of the female connector piece and the male connector piece in which the used dialysis solution flows from the peritoneal cavity into the empty bag; and FIG. 4 shows the same connecting phase as in FIG. 3 but in this position fresh dialysis solution is flowing from the full bag into the pertioneal cavity.

Figure 1:
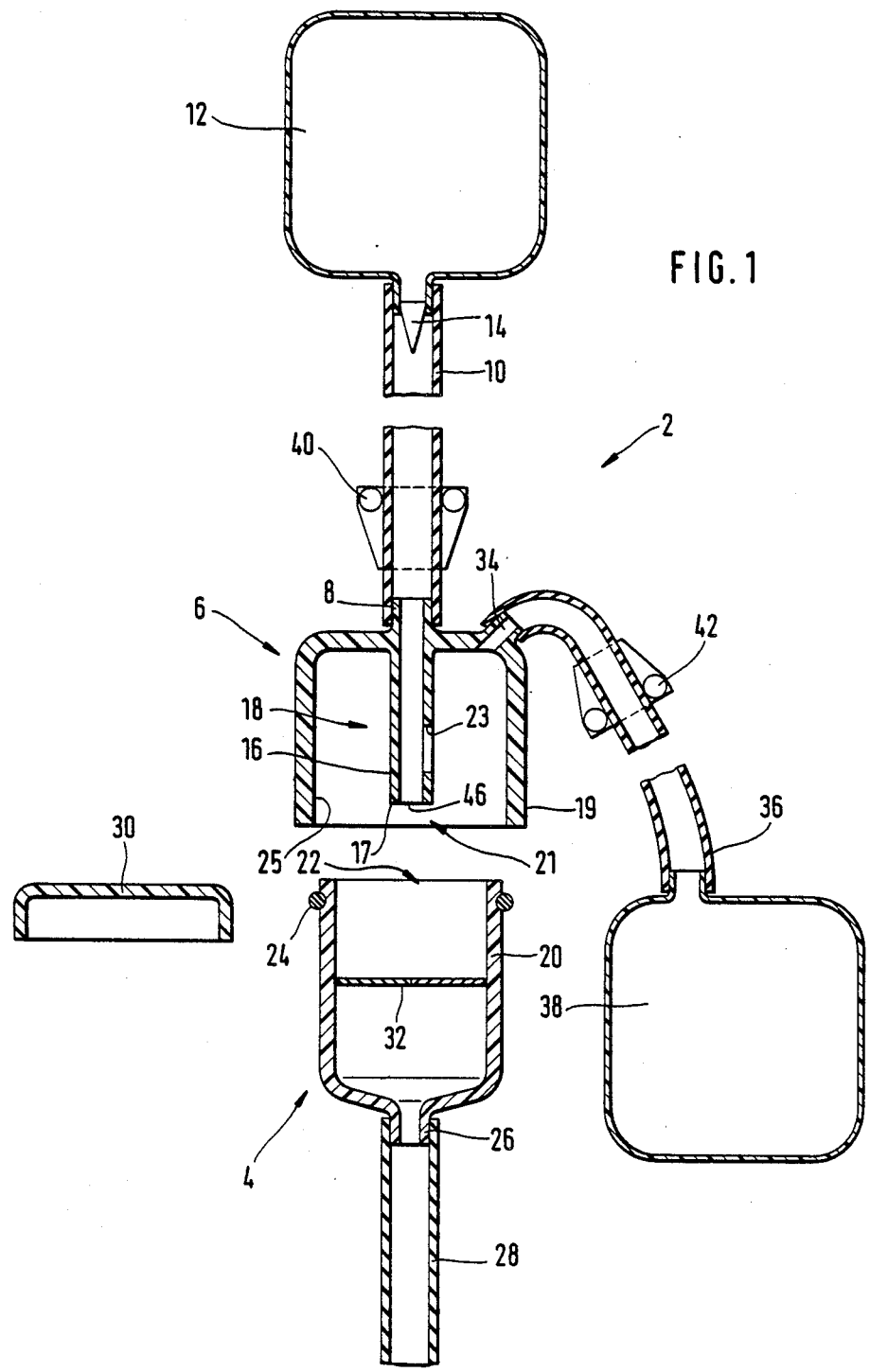
FIG. 1 is a schematical sectional view of the essential components of the two-bag system according to the invention.

As apparent from FIG. 1 a two-bag system 2 comprises essentially a female connector piece 4 and a male connector piece 6 which are shown separated from each other in FIG. 1. The male connector piece 6 is constructed as cylindrical component sealed on one side and comprises at its sealed end a first connection 8 for a supply line 10 which is connected to a bag 12 with fresh dialysis solution. In the supply line 10 in the region of the bag 12 a closure member 14 is provided which can be opened and which seals the bag with respect to the supply line and can be opened when required, for example by breaking off a breakage portion.

As apparent from the drawing, the first connection 8 extends from the outer side of the male connector piece 6 coaxially to said male connector piece 6 in the form of an inner tube section 16 into a receiving region 18 which is provided between the tube section 16 and a protective sleeve 19 which engages round and over said tube section 16. The front region 17 of the tube section 16 is spaced far enough away from the edge region of the protective sleeve to ensure that no contact is possible. Furthermore, at least one radial opening 23 is provided preferably adjacent the front region 17 of the tube section 16. The connection of the supply line 10 to the first connection 8 can be effected in usual manner by shrinking on, adhering, a Luer connection, a clamp or the like.

In accordance with FIG. 1 the female connector piece 4 comprises a hollow cylindrical introduction portion 20 comprising an introduction opening 22. The external diameter of the introduciton poriton 20 is so dimensioned that the female connection piece 4 can be introduced with slight clearance into the receiving region 18 of the male connector piece 6. To obtain a liquid-tight connection between the female connector piece 4 and the male connector piece 6 in the connected state, directly adjacent the introduction opening 22 of the female connector piece 4 an annular sealing member 24 is disposed which is constructed for example as O ring. At the side of the female connector piece 4 opposite the introduction opening 22 a second connection 26 is formed with which the female connector piece 4 is connectable via a supply line 28 to a peritoneal catheter not illustrated in the drawings. The introduction opening 22 of the female connector piece 4 is sealed with a removable cap designated by 30 in FIG. 1 when no peritoneal dialysis is being carried out. As apparent in FIG. 1, the female connector piece 4 thus has a hollow cylindrical form of substantially circular cross-section, the one end comprising the introduction opening 22 and the other end being tapered towards the tube connection 26.

Furthermore, the radial opening 23 can also extend from the front region 17 to form one or more slots in the tube section 16 to the connection 8, retaining its funtion.

In the female connection piece 4 between the introduction opening 22 thereof and the second connection 26 a closure member 32 is disposed which under adequate mechanical load opens in the direction towards the second connection 26 and frees a fluid passage from the introduction opening 22 to the second connection 26. Said closure member 32 may for example be a valve plate having a star-shaped slot as described for example in DE-OS 3,210,148 of Applicants.

The male connector piece 6 comprises a third connection 34 advantageously in the region of the first connection 8 to which a supply line 36 to an empty bag 38 is connectable or connected. The empty bag 38 serves to receive the used dialysis solution from the peritoneal cavity or to receive the flushing solution from the full bag 12. In the vicinity of the male connector piece 6 both on the supply line 10 and on the supply line 36 a shutoff member 40 and 42 respectively is disposed. Said shutoff members 40 and 42 are for example in the form of roller or pinch clamps and serve to open or shut off the fluid flow through the line 10 or the line 36 respectively.

Hereinafter, with particular reference to FIGS. 2 to 4 the use and mode of operation of the present two-bag system will be described.

When a patient must be subjected to peritoneal dialysis the cap 30 is removed from the female connector piece 4 so that the introduction opening 22 of the female connector piece 4 is exposed. The region above the closure member 32 is normally filled with a disinfectant, or the latter is injected thereinto, which prior to introduction of fresh dialysis solution is to be flushed out of the full bag 12 into the empty bag 38. For this purpose, after removal of the cap 30 from the female connector piece 4 the female connector piece 4 is introduced into a receiving opening 21 of the male connector piece 6 in such a manner that a first connection state according to FIG. 2 is reached in which the O ring 24 of the female connector piece 4 bears sealingly on the inner peripheral wall 25 of the protective sleeve 19 of the male connector piece 6 so that a closed space 44 results which is defined by the inner wall of the male connector piece 6, the O ring 24 and the closure member 32. The introduction of the female connector piece 4 into the male connector piece 6 up to the first connection state thereof shown in FIG. 2 may for example be supported and secured by a screw connection or the like not illustrated in the drawings. It is pointed out that in the first connection phase the front region 17 of the tube section 16 does not open the closure member 32.

Figure 2:
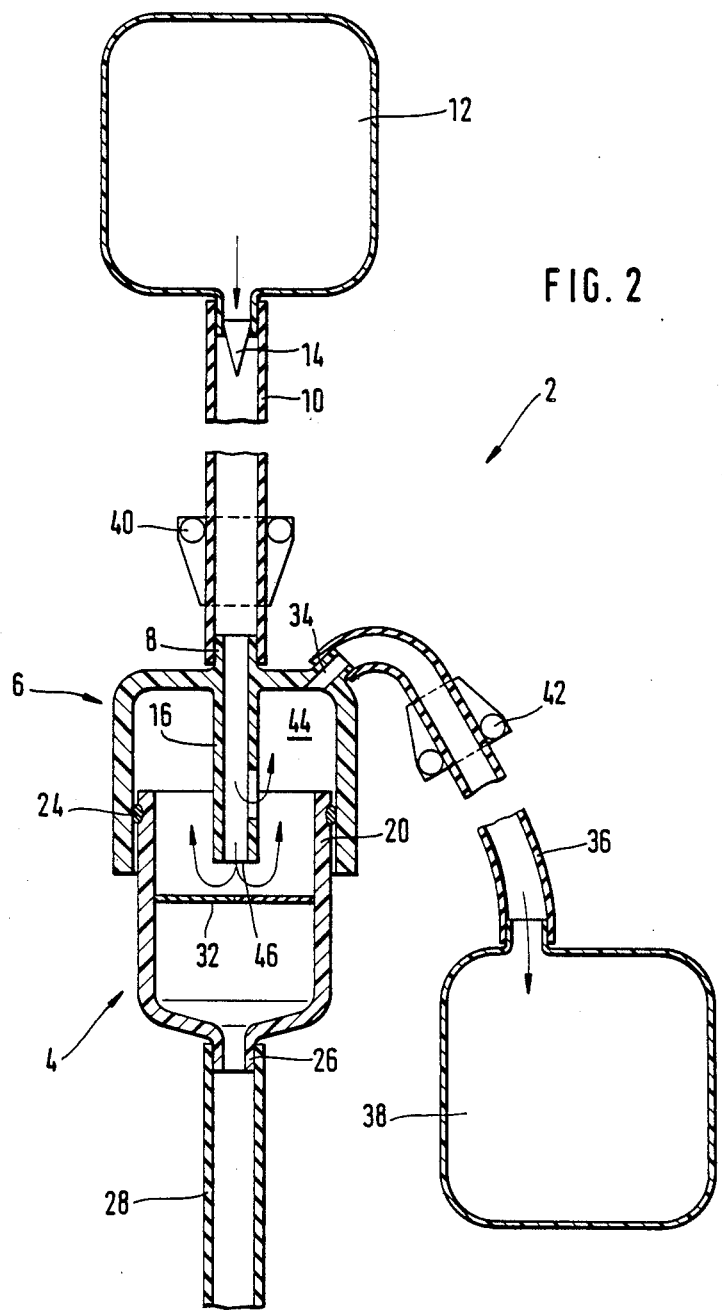
FIG. 2 shows a first connecting phase of the female connector piece and the male connector piece in which the flushing operation takes place.

Thus, in the first connection state according to FIG. 2 the inner tube 16 of the male connector piece 6 extends into the introduction opening 22 of the female connector piece 4 in such a manner that a mouth opening 46 in the tube section 16 is disposed within the introduction opening 22 and above the closure member 32.

Said first connection state according to FIG. 2 is referred to as flushing position.

Before discharge of the used dialysis solution from the peritoneal cavity into the empty bag 38 and before supplying fresh dialysis solution to the peritoneal cavity from the full bag 12 a flushing operation is carried out, in particular to remove disinfectant from the closed space 44. For this purpose the two roller clamps 40 and 42 at the supply lines 10 and 36 are opened so that a free fluid passage is established from the closure member 14 at the full bag 12 to the empty bag 38. Thereafter the full bag 12 is opened by breaking off the breakage cone portion from the closure member 14 and fresh dialysis solution flows out of the bag 12 through the supply line 10 and the inner tube 16 to the radial opening 23 and to the mouth opening 46 of the tube section 16 and through the closed space 44, the third conneciton 34 and the supply line 36 into the empty bag 38 as indicated in FIG. 2 by the flow arrows.

The disinfectant in the closed space 44 and particles formed on opening the closure member 14 are thus flushed by the fresh dialysis solution from the full bag 12 out of the closed space 44 into the empty bag 38. The effectiveness of the flushing operation is increased in that firstly the mouth opening 46 of the tube section 16 is disposed closely above the closure member 32 so that the flushing solution completely fills the closed space 44 and expels the disinfectant through the third connection 34 into the empty bag 38. On the other hand, the open diameter of the tube section 16 or the mouth openings 46 is preferably greater than the open diameter of the third connection 34 so that a pressure flushing of the closed space 44 is effected by the fresh dialysis solution from the full bag 12.

By the arrangement of the O ring 24 in the immediate vicinity of the introduciton opening 22 of the female connector piece 4, in the closed space 44 substantially no dead space and no undercutting results in which disinfectant can remain and consequently a thorough and above all a rapid flushing of the closed space 44 is ensured.

After completion of the flushing operations the used dialysis solution is drained from the peritoneal cavity of the patient. For this purpose firstly the roller clamp 40 in the supply line 10 is actuated in such a manner that the supply of fresh dialysate from the full bag 12 to the closed space 44 is interrupted. The roller clamp 44 of the supply line 36 to the empty bage 38 remains open. Thereafter the female connector piece 4 is introduced by screwing or pushing further into the receiving region 18 of the male connector piece 6 until a second connection state according to FIG. 3 is reached.

As apparent from FIG. 3 the front region 17 of the tube section 16 opens the closure member 32, the latter being forced in the direction towards the second connection 26 of the female connector piece 4. The radial opening 23 in the tube section 16 is advantageously far enough away from the front region 17 to ensure that no occupation obstructing the fluid passage is possible through the closure member 32 via the connection 34. Thus, a flow connection is established from the tubing 28 through the connection 26, the opened closure member 32, the mouth opening 46 and the radial opening 23 of the tube section 16 to the tubing 36 and the empty bag 38 or connection 8. Along this fluid passage the used dialysis solution now flows from the peritoneal cavity of the patient through the connector 2 into the empty bag 38 as illustrated in FIG. 3 by the flow arrows, the closure element 40 remaining closed.

This second conneciton state of the female connector piece 4 and the male connector piece 6 is referred to as inlet/drain position.

When the used dialysis solution has been completely drained from the peritoneal cavity of the patient, the roller clamp 42 of the supply line 36 to the empty bag 38 now filled with the used dialysis solution is closed so that the conneciton between the peritoneal cavity and the empty bag 38 is interrupted.

Then, in accordance with FIG. 4 the roller clamp 40 of the supplu line 10 is opened so that a fluid passage is freed from the full bag 12 through the male connector 6 and the female connector 4 to the peritoneal cavity of the patient. The position of the female connector 4 within the male connector 6 corresponds largely to the second connection state according to FIG. 3, i.e. the closure member 32 is open in the direction towards the second connection 26 with deformation so that the mouth opening 46 of the inner tube 16 is in flow connection with the tubing 28. Thus, fresh dialysis solution can pass unrestricted from the full bag 2 into the peritoneal cavity of the patient as indicated in FIG. 4 by the flow arrows.

When the content of the full bag 12 has flowed into the peritoneal cavity of the patient the male connector piece 6 is disconnected from the female connector piece 4, the first conenction state according to FIG. 2 then first being reached again in which the closure member 32 has again returned resiliently to its starting position so that the access to the peritoneal cavity of the patient is again closed. Thereafter the final disconnection of the female connector piece 4 from the male connector piece 6 is effected. A suitable disinfectant is introduced or injected into the free space above the closure member 32, whereupon the introduction opening 22 of the female connector piece 4 is again closed with the disinfected or sterile cap 30.

Advantageously, the full bag 12, the supply line 10, the male connector piece 6, the supply line 36 and the empty bag 38 are made and packed sterile as a unit so that no problems are encountered in keeping the male connector side germ-free. Such a unit is preferably surrounded by an evacuated protective envelope in the form of a sterile protective bag as described in European patent No. 50 255 . After use of this unit, i.e. after completing the dialysis, the male connector piece and the bags 12 and 38 connected thereto are discarded or destroyed.

In a further embodiment the central tube section 16 of the male connector piece 6 has no radial opening 23. In this case the closure member 32 opens to form a first flow connection which as mentioned above leads directly through the central tube section 16 and a second flow connection leading past said tube section 16 through forming slots and the like in the closure member 32 into the space 44.

The selection of the materials for making the two connector pieces and the corresponding supply lines is within the scope of the expert; for example, physiologically neutral plastics or metals can be used.

I claim:

1. A connector for use in peritoneal dialysis comprising:
   a first connector piece having means defining an introduction opening;
   a second connector piece having a central tube section introducible into said introduction opening of said first connector piece;
   a first connection means, on one of said two connector pieces, for connecting to a first flexible tube portion, said first flexible tube connection being connected to a first bag containing dialysis solution;
   a second connection means, on a second connector piece, for connecting to a second flexible tube portion, said second flexible tube connection being connectable to a peritoneal catheter;
   a third connection means for connecting a third flexible tube portion to a second bag;
   at least first and second clamps for clamping off the first and third flexible tube portions;
   said central tube section (16) of said second connector piece (6) engaged and surrounded by an outer sleeve (19), said first connector piece (4) surrounded on its outer surface by an annular seal (24) mating with an inner face (25) on said outer sleeve (19) forming a sealing arrangement with the interior of the connector;
   said third connection (34) originatiing from a rearward section of said outer sleeve (19);
   said central tube section (16) further comprising at least one radial opening (23);
   said first connector piece (4) further comprising a closure member (32) oriented between said introduction opening (22) and said second connection means (26) having a first connection state (FIG. 2) defining a means for flushing disinfectant and particles from said connector, a front end of said central tube section (16) oriented between closure member (32) causing a first fluid communication path between said first bag (12) through said central tube section (16), space (44) surrounding said central tube section (16) within said connector (6), and said third connection means (34) to the second bag (38);
   a second connection state (FIG. 3) having a second fluid communication path, said front end of the central tube section (16) penetrating said closure means (32) and said central tube section (16) closed by the first clamp (40) establishing a fluid connection from the supply line (28) through the central tube section (16) and said radial opening (23) to the second bag (38); and
   a third conneciton state (FIG. 4) having a third fluid communication path, said first clamp (40) on said first flexible tube portion (10) establishing a fluid conneciton between said first bag and said supply line (28) when said second clamp (42) is closed.

2. The connector of claim 1 further comprises:
   said front region (17) of the central tube section (16) positioned axially closer to a receiving opening (21) on said second connector piece (6) than said third conneciton (34).

3. The connector of claim 1 further comprises:
   a removable cap (30) sealing said introduction opening (22) on said first connector piece (4).

4. The connector of claim 1, further comprises:
   said clamps further comprising roller clamps for opening and closing the fluid flow paths in siad first flexible tube portion and in said third flexible tube portion.

5. A male coupling for use in a peritoneal dialysis connector using a two-bag system comprising:
   a flushing means for flushing disinfectant and particles from said connector comprising a central tube section surrounded and engaged by an outer sleeve having a periperal wall being in flow connection with a first connection means (8) for connecting a dialysis bag on said outer sleeve;
   said central tube section being spaced from said peripheral wall having an unobstructed flow path therethrough and terminating in an open end into the interior of said sleeve;
   at least one radial opening on said central tube section opening into the interior of said sleeve before the open end of said tube section; and
   said outer sleeve (19) having a second connection means (34) for connecting to a second dialysis bag (38) whereby a flushing solution may be introduced through said central tube section into said connector for flushing disinfectant and particles out of said connector through said second connection means.

6. A connector for use in peritoneal dialysis comprising:
   a first connector piece having means defining an introduction opening;
   a second connector piece having a central tube section introducible into said introduction opening of said first connector piece;
   a first connection means, on one of said two connector pieces, for connecting to a first flexible tube portion, said first flexible tube connection being connected to a first bag containing dialysis solution;
   a second connection means, on a second connector piece, for connecting to a second flexible tube portion, said second flexible tube connection being connectable to a peritoneal catheter;
   a third conneciton means for connecting a third flexible tube portion to a second bag;
   said central tube section (16) of said second connector piece (6) engaged and surrounded by an outer sleeve (19), said first connector piece (4) surrounded on its outer surface by an annular seal (24) mating with an inner face (25) on said outer sleeve (19) forming a sealing arrangement with the interior of the connector;
   said central tube section (16) further comprising at least one radial opening (23);
   said first connector piece (4) further comprising a closure member (32) oriented between said introduction opening (22) and said second connection means (26) having a first connection state (FIG. 2) defining a means for flushing disinfectant and particles from said connector, a front end of said central tube section (16) oriented between closure member (32) causing a first fluid communication path between said first connection means through said central tube section (16), space (44) surrounding said central tube section (16) within said connector (6), and said third connection means (34) to the second bag (38); and a second connection state (FIG. 3) having a second fluid communication path, said front end of the central tube section (16) penetrating said closure means (32) and said central tube section (16) closed by a first clamp (40) establishing a fluid connection from the supply line (28) through the central tube section (16) and said radial opening (23) to said third connection means.

* * * * *